United States Patent
Kopperschmidt

(10) Patent No.: US 8,500,671 B2
(45) Date of Patent: Aug. 6, 2013

(54) DEVICE FOR EXTRACORPOREAL BLOOD TREATMENT IN SINGLE-NEEDLE OPERATION MODE

(75) Inventor: Pascal Kopperschmidt, Dittelbrunn (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 195 days.

(21) Appl. No.: 13/122,220

(22) PCT Filed: Sep. 29, 2009

(86) PCT No.: PCT/EP2009/006994
§ 371 (c)(1),
(2), (4) Date: Apr. 1, 2011

(87) PCT Pub. No.: WO2010/037520
PCT Pub. Date: Apr. 8, 2010

(65) Prior Publication Data
US 2011/0178452 A1 Jul. 21, 2011

(30) Foreign Application Priority Data
Oct. 2, 2008 (DE) .......................... 10 2008 050 367

(51) Int. Cl.
*A61M 37/00* (2006.01)
(52) U.S. Cl.
USPC ........ 604/6.05; 604/6.11; 604/5.04; 604/6.09
(58) Field of Classification Search
USPC .................... 604/4.01, 5.01, 5.04, 6.05, 6.09, 604/6.11; 210/645
See application file for complete search history.

(56) References Cited

U.S. PATENT DOCUMENTS

| 4,231,366 A | 11/1980 | Schael |
| 4,464,164 A | 8/1984 | Troutner et al. |
| 4,758,336 A | 7/1988 | Bock et al. |
| 4,828,543 A * | 5/1989 | Weiss et al. .................. 604/6.09 |

(Continued)

FOREIGN PATENT DOCUMENTS

| DE | 26 36 290 | 2/1978 |
| DE | 39 23 836 | 9/1990 |

(Continued)

OTHER PUBLICATIONS

International Preliminary Report on Patentability from PCT/EP2009/006994 mailed on Apr. 14, 2011.

(Continued)

*Primary Examiner* — Leslie Deak
(74) *Attorney, Agent, or Firm* — Kenyon & Kenyon LLP

(57) ABSTRACT

A device for the extracorporal blood treatment in a single-needle operating mode includes means for delivering blood into, and means for delivering blood out of means for collecting blood, and a controller for setting the respective delivery rates of the means for the delivery of blood. The operating mode of the means for delivering blood is continually switched between an arterial and a venous phase by the controller, wherein during the arterial phase the delivery rate $Q_b$ of the means for delivering blood is greater than the delivery rate $Q_{sn}$ of the means for delivering blood such that blood may be withdrawn from the patient during the arterial phase, and during the venous phase the delivery rate $Q_b$ is smaller than the delivery rate $Q_{sn}$ such that blood may be administered to the patient during the venous phase.

16 Claims, 1 Drawing Sheet

(56) References Cited

U.S. PATENT DOCUMENTS

| | | | |
|---|---|---|---|
| 4,904,234 A | 2/1990 | Shimomura et al. | |
| 5,098,373 A | 3/1992 | Polaschegg | |
| 2004/0199098 A1 | 10/2004 | Pierce et al. | |

FOREIGN PATENT DOCUMENTS

| | | |
|---|---|---|
| DE | 40 39 084 | 6/1992 |
| EP | 0 229 271 | 7/1987 |
| WO | WO 94/08687 | 4/1994 |

OTHER PUBLICATIONS

PCT International Search Report for PCT/EP2009/006994 mailed on Feb. 1, 2010.

* cited by examiner

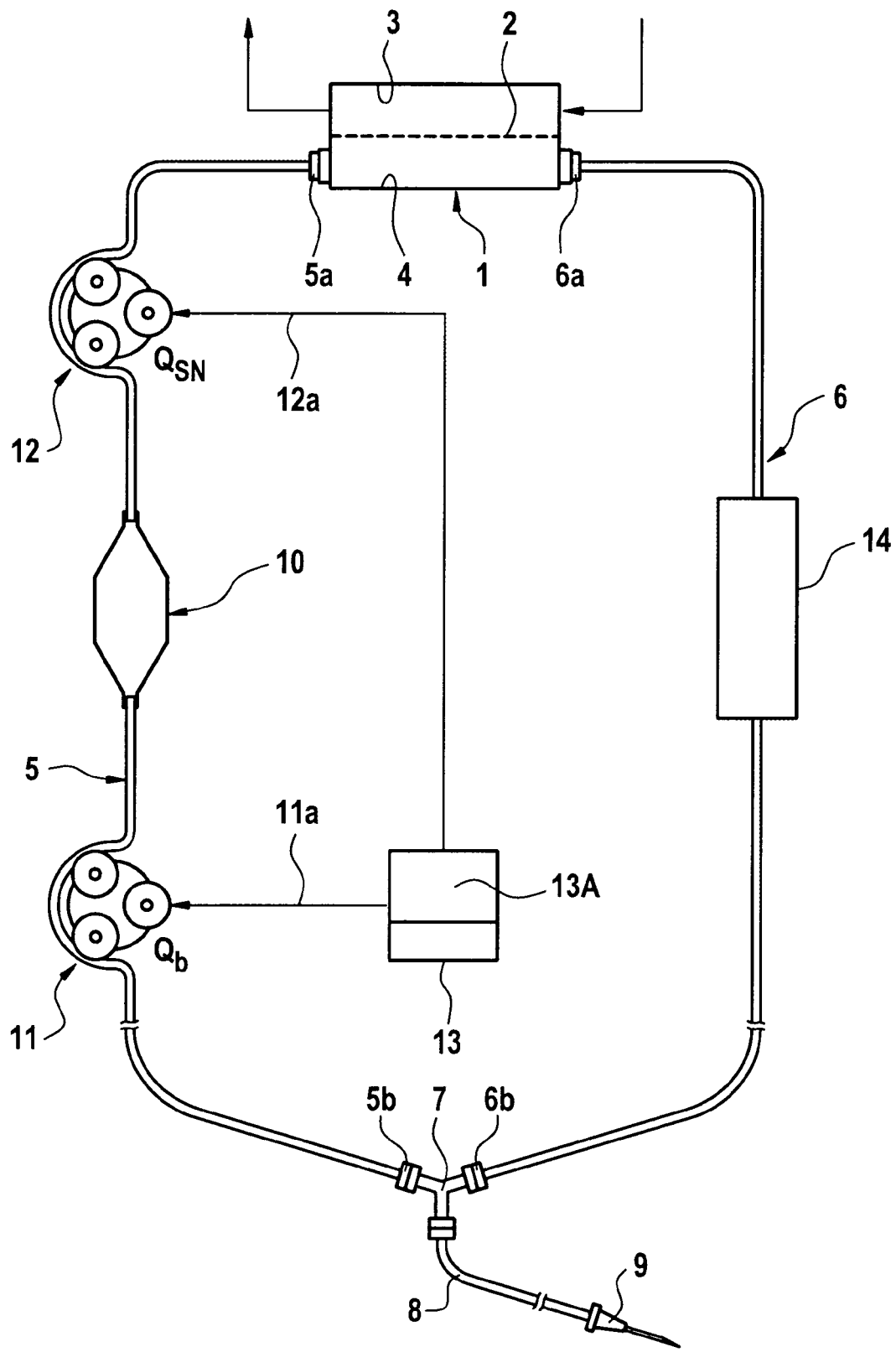

DEVICE FOR EXTRACORPOREAL BLOOD TREATMENT IN SINGLE-NEEDLE OPERATION MODE

FIELD OF THE INVENTION

The present invention relates to an apparatus for extracorporeal blood treatment in the single-needle operation, wherein blood is removed from a patient in an arterial phase and the blood is fed back to the patient in a venous phase. Moreover, the present invention relates to a method for extracorporeal blood treatment in the single-needle operation.

BACKGROUND

Extracorporeal blood treatment apparatuses with a blood treatment unit through which a patient's blood flows are generally known. These include, for example, the known hemodialysis, hemofiltration or hemodiafiltration apparatuses. The known blood treatment apparatuses can be operated in the single-needle or double-needle operation.

With the single-needle operation, the blood is removed from the patient with a single needle, conveyed into the blood treatment unit of the blood treatment apparatus and fed back to the patient via a single needle. The blood removed from the patient is stored in a reservoir during an arterial phase and is fed back to the patient from the reservoir in a venous phase. The blood flows through the blood treatment unit of the blood treatment apparatus.

For the removal and return of the blood, use is made of replaceable blood hose systems with a blood supply line and blood return line, to which the single needle (cannula) is connected. The replaceable hose systems are put into the blood treatment apparatus and disposed of after the blood treatment. These hose systems are also referred to as disposables. The blood treatment unit is also generally intended for one-off use.

Blood treatment apparatuses for the single-needle operation are known which comprise only a single blood pump, which is disposed in the arterial blood supply line. For the collection of the blood, a blood reservoir which has a sufficient compliance is located upstream or downstream of the blood treatment unit. Apart from the blood treatment apparatuses for the single-needle operation with only a single blood pump, blood treatment apparatuses are also known which comprise two blood pumps, whereof one is disposed in the arterial blood supply line upstream of the blood reservoir and the other pump is disposed in the blood supply line leading to the blood treatment unit downstream of the blood reservoir. These two pumps are operated alternately in the arterial and venous phase. In the arterial phase, the blood removed from the patient is conveyed by the first blood pump into the blood reservoir, whilst in the venous phase the blood collected in the blood reservoir is conveyed to the patient by the second blood pump. The blood thereby flows through the dialyzer. It is crucial that the second blood pump is stationary during the operation of the first blood pump and that the first blood pump is stationary during the operation of the second blood pump. The blood supply line is therefore interrupted respectively upstream or downstream of the blood reservoir. A compliance of the blood reservoir is not required in the case of operation with two pumps.

Blood treatment apparatuses for the single-needle operation with one or two blood pumps are described for example in the specialist book "Replacement of Renal Function by Dialysis", 5$^{th}$ Revised Edition, ISBN 1-4020-0083-9, Kluwer Academic Publishers pages 365-367.

A dialysis apparatus for the single-needle operation is known from German Patent Publication No. DE 196 33 657 C1, which comprises a blood pump disposed in the arterial blood line, the blood reservoir comprising a blood bag disposed in the arterial blood line and a blood bag disposed in the venous blood line. Pressure is applied with a device to both blood bags, so that blood can be conveyed out of the blood bags.

Small children and infants who are suffering from kidney failure are treated with only relatively small blood flows on account of their small body volume. Dialysis treatments with continuous blood flows which are relatively small, for example lying at approximately 5 ml/min, are generally not possible with blood treatment apparatuses comprising conventional blood pumps, since the internal control for the stabilization of the motor revolutions requires a defined minimum rotational speed for the pump rotor in order to guarantee a jerk-free operation. This results in a minimum blood flow of approx. 20 ml/min. This blood flow, however, is too great for patients with a low body weight, for example a body weight of 10 kg.

In view of the aforementioned problems, a goal underlying the present invention is to provide an apparatus for extracorporeal blood treatment in the single-needle operation, which also enables a blood treatment with relatively small blood flows.

A further goal of the present invention is to specify a method for extracorporeal blood treatment in the single-needle operation, which enables a blood treatment with relatively small blood flows.

SUMMARY

Example apparatuses according to the present invention for extracorporeal blood treatment and the example methods according to the present invention for extracorporeal blood treatment in the single-needle operation are characterized in that, during the arterial and venous phase, blood is conveyed both into the means for collecting blood and blood is conveyed out of the means for collecting blood. The example apparatuses according to the present invention and the example methods according to the present invention do not therefore provide an alternating operation of the means for conveying blood, but rather the simultaneous operation of the means for conveying blood in the arterial and venous phase.

The simultaneous operation of both means for conveying blood permits the selection of different delivery rates. In the arterial phase, the delivery rate of the means for conveying blood into the means for collecting blood is adjusted in such a way that this delivery rate is greater than the delivery rate of the means for conveying blood out of the means for collecting blood. Blood is therefore removed from the patient in the arterial phase. In the venous phase, on the other hand, the delivery rate of the means for conveying blood into the means for collecting blood is smaller than the delivery rate of the means for conveying blood out of the means for collecting blood. Blood is thus fed to the patient in the venous phase.

The effective delivery rate results from the difference between two types of delivery. Since it concerns only the difference between the delivery rates, the means for conveying blood can be operated at relatively large delivery rates, even if the effective delivery rate is relatively small. The use of blood pumps, in particular peristaltic blood pumps, for example roller pumps, is thus possible in order to enable a blood treatment to be carried out at a relatively small blood flow rate. Conventional blood pumps, whose minimum flow rate lies above the desired blood flow, can therefore also be used.

A further advantage consists in the fact that relatively small dialyzers or filters can be used, since a high flow prevails in the extracorporeal blood circuit and the blood is pumped repeatedly through the dialyzer or filter (recirculation). The flow from the patient and to the patient, however, is nonetheless small.

The means for conveying blood can be constituted in different ways. Preferably, the means for conveying blood are blood pumps. Blood bags, upon which pressure is exerted, can however also be used for conveying blood. Such an arrangement is known for example from German Patent Publication No. DE 196 33 657 C1.

The amount of the difference between the delivery rate of the means for conveying blood into the means for collecting blood and the delivery rate of the means for conveying blood out of the means for collecting blood is preferably the same in the arterial phase and in the venous phase. It is, however, also possible for the amount of the difference between the delivery rate of the means for conveying blood into the means for collecting blood and the delivery rate of the means for conveying blood out of the means for collecting blood to be different in the arterial phase and in the venous phase.

The means for collecting blood can be constituted in different ways. For example, the means for collecting blood can be a blood container, in particular a blood bag. A sufficient compliance is however not required, since the blood is conveyed with two pumps.

In a special embodiment of the extracorporeal blood treatment apparatus, a mixture of plasma and soluble components can be removed from the blood. For this purpose, a pressure gradient between the blood chamber and the dialyzing fluid chamber of the blood treatment unit is built up by suitable means, as a result of which a substance transfer from the blood via the semipermeable membrane into the dialysate takes place. This process is referred to as ultrafiltration (source: Die Dialysefibel 3 S786, ISBN 978-3-939508-88-5). The fluid loss of the blood can be compensated for wholly, partially or excessively by the addition of a substituate solution. This process is referred to as postdilution when the addition of the substituate solution takes place downstream of the blood treatment unit, or predilution when the addition of the substituate solution takes place upstream of the blood treatment unit.

A preferred embodiment of the extracorporeal blood treatment apparatus comprises an input unit for inputting an effective blood flow, which can be relatively small in order to enable a blood treatment to be carried out in the case of small children or infants. The control unit of the blood treatment apparatus is designed in such a way that the delivery rate of the means for conveying blood into the means for collecting blood and the delivery rate of the means for conveying blood out of the means for collecting blood are adjusted in such a way that, in the venous phase, the difference between the delivery rate of the means for conveying blood out of the means for collecting blood and the delivery rate of the means for conveying blood into the means for collecting blood is equal to the predetermined effective blood flow.

An alternative preferred embodiment of the extracorporeal blood treatment apparatus comprises an input unit for inputting the effective blood flow, which can be relatively small, in the arterial phase and for inputting another effective blood flow in the venous phase, which can be relatively small and differs from the effective blood flow in the arterial phase. The control unit of the blood treatment apparatus is designed in such a way that the delivery rate of the means for conveying blood into the means for collecting blood and the delivery rate of the means for conveying blood out of the means for collecting blood are adjusted in such a way that, in the arterial phase, the difference between the delivery rate of the means for conveying blood into the means for collecting blood and the delivery rate of the means for conveying blood out of the means for collecting blood is equal to the predetermined effective blood flow of the arterial phase, and in the venous phase is equal to the predetermined effective blood flow of the venous phase.

The blood treatment unit and the blood line system, which comprises an arterial blood supply line leading to the blood treatment unit and a venous blood return line leading away from the blood treatment unit, are preferably not a fixed component of the extracorporeal blood treatment apparatus, but are rather intended for one-off use.

In another preferred embodiment, the means for storing blood are disposed in the arterial blood supply line, which leads to the blood treatment unit of the extracorporeal blood treatment apparatus, especially the dialyzer. In principle, however, it is also possible for the means for storing blood to be disposed in the venous blood line, which leads away from the blood treatment unit, especially the dialyzer. The only crucial factor is that the means for collecting blood are disposed between the means for conveying blood into the means for collecting blood and the means for conveying blood out of the means for collecting blood, the relative position of the blood treatment unit not being relevant.

An example embodiment of the present invention is explained below in greater detail by reference to the single FIGURE.

BRIEF DESCRIPTION OF THE DRAWING

The single FIGURE shows, in a very simplified schematic representation, an extracorporeal blood treatment apparatus for the single-needle operation.

DETAILED DESCRIPTION

For the sake of greater clarity, only the components of the example blood treatment apparatus essential to the present invention are represented in the FIGURE.

The blood treatment apparatus, which can be a hemodialysis apparatus, comprises as a blood treatment unit a dialyzer 1, which is divided by a semipermeable membrane 2 into a dialyzing fluid chamber 3 and a blood chamber 4. Only extracorporeal blood circuit I is represented in the FIGURE, the dialyzing fluid circuit of the hemodialysis apparatus being indicated solely by an arrow.

A disposable is placed into the blood treatment apparatus, said disposable comprising an arterial blood supply line 5 with two hose connections 5a and 5b, a blood return line 6 with two hose connections 6a and 6b, a T-connection piece 7, a common hose line 8, and a needle (hollow cannula) 9. Blood supply line 5 is connected at one end to inlet 5a of blood chamber 4 of dialyzer 1 and to one connection branch of T-connection piece 7 at the other end, whilst blood return line 6 is connected at one end to outlet 6a of blood chamber 4 of dialyzer 1 and to the other connection branch of T-connection piece 7 at the other end. The common connection branch of T-connection piece 7 is connected via common blood line 8 to needle 9, which is inserted into a blood vessel of the patient.

Incorporated into arterial blood supply line 5 are means 10 for collecting blood, which are designed as rigid containers.

Blood collection container 10 is a component of the blood hose system. A bubble trap 14 (drip chamber) is located in venous blood return line 6.

The patient's blood is conveyed by first means 11 into blood collection container 10, whilst the blood is conveyed from collection container 10 by second means 12. The two means 11 and 12 for conveying blood are peristaltic blood pumps, in particular roller pumps, into which arterial blood line 5 is inserted. Both blood pumps 11 and 12 are connected via control lines 11a, 12a to a central control unit 13 of the blood treatment apparatus, which selects a specific delivery rate $Q_b$, $Q_{SN}$ respectively for blood pump 11 upstream of blood collection container 10 and blood pump 12 downstream of blood collection container 10.

Central control unit 13 of the blood treatment apparatus is designed in such a way that the operation of blood pumps 11 and 12 during the extracorporeal blood treatment is continuously switched over between an arterial and a venous phase. In the arterial phase, control unit 13 adjusts a delivery rate $Q_{ba}$ for pump 11 upstream of collection container 10 and a delivery rate $Q_{SNa}$ for pump 12 downstream of collection container 10, delivery rate $Q_{ba}$ being greater than delivery rate $Q_{SNa}$. In the venous phase, which immediately follows the arterial phase, control unit 13 selects a delivery rate $Q_{bv}$ for pump 11 upstream of container 10 and a delivery rate $Q_{SNv}$ for pump 12 downstream of container 10, delivery rate $Q_{bv}$ being smaller than delivery rate $Q_{SNv}$. The difference between delivery rate $Q_{ba}$ of pump 11 upstream of container 10 and delivery rate $Q_{SNa}$ of pump 12 downstream of container 10 in the arterial phase is the effective arterial blood flow rate $Q_{effa}$ with which the blood treatment is to be carried out in the arterial phase. The difference between delivery rate $Q_{SNv}$ of pump 12 downstream of container 10 and delivery rate $Q_{bv}$ of pump 11 upstream of container 10 in the venous phase is the effective venous blood flow rate $Q_{effv}$ with which the blood treatment is to be carried out in the venous phase. In a preferred embodiment, the duration of the arterial and venous phase is equal, but the duration of the arterial and venous phase may also be different.

Control unit 13 comprises an input unit 13A, with which effective blood flow rates $Q_{effa}$ of the arterial phase and $Q_{effv}$ of the venous phase are adjusted. In addition, values for the SN pump flow $Q_{SNa}$ and $Q_{SNv}$ or values for blood pump flows $Q_{ba}$ and $Q_{bv}$, and the value for the blood volume which is removed from the blood vessel in the arterial phase $V_{SN}$ can be inputted into input unit 13A.

Depending on the level of equipment of the blood treatment apparatus, values for the ultrafiltration and the dilution of the substituate solution can also be inputted. Control unit 13 calculates from these inputs the control signals for the means for conveying blood and for the means which bring about the ultrafiltration and the substituate dilution.

With an exemplary embodiment of the blood treatment apparatus without ultrafiltration and substituate dilution and the inputs into control unit 13A $Q_{ba}$=55 ml/min, $Q_{bv}$=50 ml/min, $Q_{effa}$=5 ml and $Q_{effv}$=−5 ml, control unit 13 adjusts delivery rates $Q_{ba}$ and $Q_{SNa}$ in such a way that $Q_{ba}$=55 ml/min and $Q_{SNa}$=50 ml/min in the arterial phase and therefore the difference between delivery rates $Q_{eff}=Q_{ba}-Q_{SNa}$=5 ml/min is positive, which signifies a blood flow from cannula 9 out of the blood vessel into the extracorporeal blood circuit. For the venous phase, control unit 13A adjusts delivery rates $Q_{bv}$=50 ml/min and $Q_{SNv}$=55 ml/min, so that the difference between delivery rates $Q_{eff}=Q_{ba}-Q_{SNa}$=−5 ml/min is negative, which signifies a blood flow out of the extracorporeal blood circuit via cannula 9 into the blood vessel.

Control unit 13 controls the duration of the individual phases, in such a way that the previously inputted values for volume $V_{SN}$, the ultrafiltration and the substituate dilution are adjusted.

The switch-over points between the arterial and venous phase can be ascertained on the basis of monitoring the pressure in blood collection container 10.

It is advantageous if one of the two blood pumps 11 and 12 is operated at a constant delivery rate, whilst the delivery rate of the other blood pump in the arterial and venous phase is in each case changed in such a way that the desired blood flows are adjusted. The change in the blood flow of only one of the two pumps requires a smaller outlay for the control of the pumps than when the delivery rates of the two pumps are changed in the respective phases.

The invention claimed is:

1. An apparatus for extracorporeal blood treatment in a single-needle operation, comprising:
   a first blood-conveyance device configured to convey blood into a blood-collection device;
   a second blood-conveyance device configured to convey blood out of the blood-collection device; and
   a control unit configured to adjust a delivery rate $Q_b$ of the first blood-conveyance device and a delivery rate $Q_{SN}$ of the second blood-conveyance device,
   wherein the control unit is configured such that the operation of the first and second blood-conveyance devices is continuously switched over between an arterial phase and a venous phase, whereby in the arterial phase during simultaneous operation of the first and second blood-conveyance devices, the delivery rate $Q_b$ of the first blood-conveyance device is greater than the delivery rate $Q_{SN}$ of the second blood-conveyance device, such that blood is removed from the patient in the arterial phase, and in the venous phase during simultaneous operation of the first and second blood-conveyance devices, the delivery rate $Q_b$ of the first blood-conveyance device is smaller than the delivery rate $Q_{SN}$ of the second blood-conveyance device, such that blood is fed to the patient in the venous phase.

2. The apparatus according to claim 1, wherein the control unit is configured such that the amount of the difference between the delivery rate $Q_b$ of the first blood-conveyance device and the delivery rate $Q_{SN}$ of the second blood-conveyance device is the same in the arterial phase and in the venous phase.

3. The apparatus according to claim 2, further comprising an input unit configured for inputting a predetermined effective blood flow $Q_{eff}$ with which the blood treatment is to be carried out, the control unit being configured such that the delivery rate $Q_b$ of the first blood-conveyance device and the delivery rate $Q_{SN}$ of the second blood-conveyance device are adjusted in such a way that, in the venous phase, the difference between the delivery rate $Q_b$ of the second blood-conveyance device and the delivery rate $Q_{SN}$ of the first blood-conveyance device is equal to the predetermined effective blood flow $Q_{eff}$.

4. The apparatus according to claim 1, wherein the control unit is configured such that the amount of the difference between the delivery rate $Q_b$ of the first blood-conveyance device and the delivery rate $Q_{SN}$ of the second blood-conveyance device is different in the arterial phase and in the venous phase.

5. The apparatus according to claim 4, further comprising an input unit configured for inputting an effective arterial blood flow $Q_{effa}$ and an effective venous blood flow $Q_{effv}$ with which the blood treatment is to be carried out, the control unit being configured such that the delivery rate $Q_b$ of the first blood-conveyance device and the delivery rate $Q_{SN}$ of the second blood-conveyance device are adjusted in such a way that, in the arterial phase, the difference between the delivery rate $Q_b$ of the first blood-conveyance device and the delivery rate $Q_{SN}$ of the second blood-conveyance device is equal to a predetermined effective arterial blood flow $Q_{effa}$ and, in the venous phase, the difference between the delivery rate $Q_{SN}$ of the second blood-conveyance device and the delivery rate $Q_b$ of the first blood-conveyance device is equal to a predetermined effective venous blood flow $Q_{effv}$.

6. The apparatus according to claim 1, further comprising:
a blood treatment unit having a blood chamber having an inlet and an outlet; and
a blood line system, wherein the blood line system comprises an arterial blood line, which leads from a needle to the inlet of the blood chamber of the blood treatment unit, and a venous blood line, which leads from the blood chamber of the blood treatment unit to the needle.

7. The apparatus according to claim 6, wherein the blood-collection device is disposed in the arterial blood line.

8. The apparatus according to claim 1, wherein the first blood-conveyance device is a blood pump.

9. The apparatus according to claim 8, wherein the blood pump is a peristaltic blood pump.

10. The apparatus according to claim 1, wherein the second blood-conveyance device is a blood pump.

11. The apparatus according to claim 10, wherein the blood pump is a peristaltic blood pump.

12. A method for operating an apparatus for extracorporeal blood treatment in a single-needle operation, comprising:
conveying blood, in an arterial phase, from a needle to a blood-collection device; and
conveying blood, in a venous phase, out of the blood-collection device to the needle,
wherein
in the arterial and venous phase, blood is conveyed simultaneously both from the needle to the blood-collection device as well as from the blood-collection device to the needle,
in the arterial phase, a delivery rate $Q_b$ at which blood is conveyed from the needle to the blood-collection device is greater than a delivery rate $Q_{SN}$ at which blood is conveyed from the blood-collection device to the needle, and
in the venous phase, the delivery rate $Q_b$ at which blood is conveyed from the needle to the blood-collection device is smaller than the delivery rate $Q_{SN}$ at which blood is conveyed from the blood-collection device to the needle.

13. The method according to claim 12, wherein the amount of the difference between the delivery rate $Q_b$ at which blood is conveyed to the blood-collection device and the delivery rate $Q_{SN}$ at which blood is conveyed from the blood-collection device to the needle is the same in the arterial phase and in the venous phase.

14. The method according to claim 13, wherein, with a predetermined effective blood flow $Q_{eff}$ in the venous phase, blood is conveyed at a delivery rate $Q_{bv}$ from the needle to the blood-collection device and blood is conveyed at a delivery rate $Q_{SNv}$ from the blood-collection device to the needle in such a way that, in the venous phase, the difference between the delivery rate $Q_{SNv}$ at which blood is conveyed from the blood-collection device to the needle and the delivery rate $Q_{bv}$ at which blood is conveyed from the needle to the blood-collection device is equal to the predetermined effective blood flow $Q_{eff}$.

15. The method according to claim 12, wherein the amount of the difference between the delivery rate $Q_b$ at which blood is conveyed to the blood-collection device and the delivery rate $Q_{SN}$ at which blood is conveyed from the blood-collection device to the needle is different in the arterial phase and in the venous phase.

16. The method according to claim 15, wherein, with a predetermined effective arterial blood flow $Q_{effa}$ in the arterial phase and with a predetermined effective venous blood flow $Q_{effv}$ in the venous phase, blood is conveyed, at a delivery rate $Q_{ba}$ in the arterial phase and a delivery rate $Q_{bv}$ in the venous phase, from the needle to the blood-collection device, and blood is conveyed, at a delivery rate $Q_{SNa}$ in the arterial phase and a delivery rate $Q_{SNv}$ in the venous phase, from the blood-collection device to the needle in such a way that, in the arterial phase, the difference between the delivery rate $Q_{bv}$ at which blood is conveyed from the needle to the blood-collection device and the delivery rate $Q_{SNa}$ at which blood is conveyed from the blood-collection device to the needle is equal to the predetermined effective arterial blood flow $Q_{effa}$, and in the venous phase the difference between the delivery rate $Q_{SNv}$ at which blood is conveyed from the blood-collection device to the needle and the delivery rate $Q_{bv}$ at which blood is conveyed from the needle to the blood-collection device is equal to the predetermined effective venous blood flow $Q_{effv}$.

* * * * *